US010988527B2

(12) United States Patent
Park et al.

(10) Patent No.: US 10,988,527 B2
(45) Date of Patent: Apr. 27, 2021

(54) METHOD FOR PREPARING TNFR-FC FUSION PROTEIN CONTAINING TARGET CONTENT OF IMPURITIES

(71) Applicant: LG CHEM, LTD., Seoul (KR)

(72) Inventors: Sang Woo Park, Daejeon (KR); Hwa Young Lee, Daejeon (KR); Soon Woong Choi, Daejeon (KR); Chul Ho Jung, Daejeon (KR)

(73) Assignee: LG CHEM, LTD., Seoul (KR)

( * ) Notice: Subject to any disclaimer, the term of this patent is extended or adjusted under 35 U.S.C. 154(b) by 26 days.

(21) Appl. No.: 15/541,111

(22) PCT Filed: Dec. 29, 2015

(86) PCT No.: PCT/KR2015/014393
§ 371 (c)(1),
(2) Date: Jun. 30, 2017

(87) PCT Pub. No.: WO2016/108569
PCT Pub. Date: Jul. 7, 2016

(65) Prior Publication Data
US 2017/0369553 A1 Dec. 28, 2017

(30) Foreign Application Priority Data
Dec. 31, 2014 (KR) .................. 10-2014-0195766

(51) Int. Cl.
C07K 1/16 (2006.01)
C07K 14/715 (2006.01)
C07K 16/00 (2006.01)
C07K 19/00 (2006.01)
C07K 14/705 (2006.01)

(52) U.S. Cl.
CPC ............ C07K 14/7151 (2013.01); C07K 1/16 (2013.01); C07K 14/705 (2013.01); C07K 14/70578 (2013.01); C07K 16/00 (2013.01); C07K 19/00 (2013.01); C07K 2319/30 (2013.01)

(58) Field of Classification Search
None
See application file for complete search history.

(56) References Cited

U.S. PATENT DOCUMENTS

| | | | |
|---|---|---|---|
| 7,294,481 B1 | 11/2007 | Fung | |
| 9,279,014 B2 * | 3/2016 | Won | C07K 14/7151 |
| 2008/0230478 A1 * | 9/2008 | Johansson | B01D 15/203 |
| | | | 210/656 |
| 2013/0101584 A1 | 4/2013 | Manning et al. | |
| 2014/0072560 A1 | 3/2014 | Arakawa et al. | |
| 2014/0128577 A1 | 5/2014 | Kulkarni et al. | |

FOREIGN PATENT DOCUMENTS

| | | |
|---|---|---|
| CN | 102382190 A | 3/2012 |
| JP | 2014-521364 A | 8/2014 |
| JP | 2014-530254 A | 11/2014 |
| KR | 10-2012-0118013 A | 10/2012 |
| KR | 10-2013-0020644 A | 2/2013 |
| KR | 10-2014-0043934 A | 4/2014 |
| KR | 10-2014-0083037 A | 7/2014 |
| WO | 2008/087184 A2 | 7/2008 |
| WO | 2012/115904 A2 | 8/2012 |
| WO | 2013/025079 A1 | 2/2013 |
| WO | 2014/102814 A1 | 7/2014 |

OTHER PUBLICATIONS

Office Action issued for New Zealand Patent Application No. 733388 dated Nov. 30, 2017, 7 pages.
Cho, et al., "Evaluation of the structural, physicochemical, and biological characteristics of SB4, a biosimilar of etanercept", mAbs. 2016 vol. 8, No. 6, pp. 1136-1155.
Office Action issued for Russian Patent Application No. 2017124181/10 dated Apr. 18, 2018, 7 pages.
Extended Search Report issued for European Patent Application No. 15875663.5 dated May 24, 2018, 9 pages.
Office Action issued for New Zealand Patent Application No. 733388 dated Jun. 25, 2018, 6 pages.
A.V. Karabel'skii, et al., "Purification of the chimeric protein Alburon16 from a culture medium of the yeast Pichia pastoris", Applied Biochemistry and Microbiology, 2012, vol. 48, No. 4, pp. 416-420.
Evans et al., "Purification of an Fc-fusion biologic: Clearance of multiple product related impurities by hydrophobic interaction chromatography" Journal of Chromatograph A, vol. 1177, pp. 265-271 (2008).
Search Report and Written Opinion issued for International Application No. PCT/KR2015/014393 dated Apr. 14, 2016 (7 pages).
Office Action issued for Japanese Patent Application No. 2017-535373 dated Jul. 9, 2018, 4 pages.

* cited by examiner

Primary Examiner — Thomas S Heard
(74) Attorney, Agent, or Firm — Rothwell, Figg, Ernst & Manbeck, P.C.

(57) ABSTRACT

The present invention relates to a method for preparing a TNFR-Fc fusion protein mixture comprising a target content of hydrophobic chromatogram peak 3, and to a method for adjusting a content of hydrophobic chromatogram peak 3. Specifically, the present invention relates to (a) a method for preparing a TNFR-Fc fusion protein mixture using a hydrophobic interaction chromatograph medium containing an aromatic functional group, which is pre-equilibrated with an equilibration buffer comprising sodium chloride or ammonium sulfate, and a sample comprising a TNFR-Fc fusion protein mixture liquid produced from mammalian cells, and to a method for adjusting the content of hydrophobic chromatogram peak 3 by hydrophobic chromatography using an equilibration buffer containing a predetermined concentration of sodium chloride or ammonium sulfate.

12 Claims, 1 Drawing Sheet

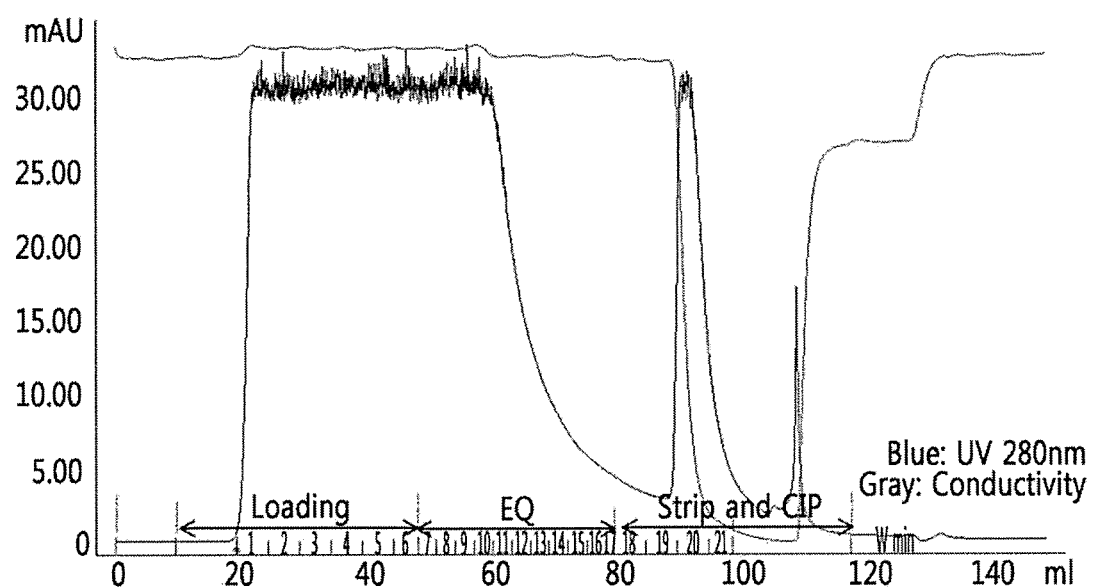

METHOD FOR PREPARING TNFR-FC FUSION PROTEIN CONTAINING TARGET CONTENT OF IMPURITIES

CROSS-REFERENCE TO RELATED APPLICATIONS

This application is a 35 U.S.C. § 371 National Phase Entry Application from PCT/KR2015/014393, filed on Dec. 29, 2015, and designating the United States, which claims priority under 35 U.S.C. § 119 to Korean Patent Application No. 10-2014-0195766, filed on Dec. 31, 2014, the entire disclosures of which are incorporated herein by reference.

TECHNICAL FIELD

The present invention relates to a method for preparing a TNFR-Fc fusion protein mixture containing a target content of hydrophobic chromatogram peak 3, and to a method for adjusting a content of hydrophobic chromatogram peak 3. Specifically, the present invention relates to (a) a method for preparing a TNFR-Fc fusion protein mixture using a hydrophobic interaction chromatograph medium containing an aromatic functional group, which is pre-equilibrated with an equilibration buffer comprising sodium chloride or ammonium sulfate, and a sample containing a TNFR-Fc fusion protein mixture liquid produced from mammalian cells, and to a method for adjusting the hydrophobic chromatogram peak 3 content by hydrophobic interaction chromatography using an equilibration buffer containing a predetermined concentration of sodium chloride or ammonium sulfate.

BACKGROUND ART

Etanercept is a biological inflammation modulator that functions as a competitive inhibitor of TNF-α, binding to cell surface TNF-α receptor, to inhibit TNF-α mediated immune responses. Etanercept is a macromolecule with a molecular weight of 150 kDa, and is a homodimer of two fusion proteins linked by disulfide bond, and each fusion protein consisting of a human soluble p75 TNF (tumor necrosis factor) receptor coupled to the Fc portion of human immunoglobulin G subclass 1 (Goldenberg, *Clinical Therapeutics*, 21(1): 75-87, 1999; Moreland et al., *Ann. Intern. Med.*, 130(6): 478-486, 1999).

The typical form of such fusion protein was first synthesized in the early 1990s by Bruce A. Beutler et al., at the University of Texas Southwestern Medical Center, and marketed by Amgen under the trade name of Enbrel® in 2002. Etanercept is a TNF-α inhibitor used to treat rheumatoid arthritis, psoriasis, and ankylosing spondylitis, and is under clinical trials for the treatment of vasculitis, Alzheimer's disease, and Crohn's disease.

The TNFR-Fc fusion protein can be prepared by fusing 235 amino acids of TNFR and 232 amino acids of Fc region, and when producing gene recombination technology, it exists in the form of a dimer and exhibits biological activity. TNFR is divided into 4 domains and a transmembrane region, and among the 235 amino acids consisting the same, the number of cysteine is 22, and such cysteine all forms disulfide bonds to form a three-dimensional structure. However, when TNFR-Fc is produced from animal cells, cysteines bind with each other at random, and thus they do not form disulfide bonds identical to those of a native protein. TNFR may be also partially truncated, and fail to form a correct TNFR-Fc dimer. TNFR-Fc with incorrect disulfide bonds cannot show the proper biological activity due to a drastic reduction in the binding ability to TNF-α. Further, when the entirety or a part of TNFR is truncated, it may also not exhibit such biological activity.

Therefore, when the TNFR-Fc dimers are produced using a recombinant DNA technology and an animal cell culture technique, active proteins, inactive proteins with incorrect disulfide bonds, aggregates, and truncated forms are produced at the same time, and thus a technique for isolating and purifying the proteins is needed.

Further, according to U.S. Pat. No. 7,294,481, whose applicant is Immunex Corporation, the developer of etanercept, and which relates to a method for producing recombinant proteins, it was confirmed that three peaks are present by hydrophobic interaction chromatography (HIC), and it was confirmed that the peaks are sequentially constituted of etanercept of various forms having a very low biological activity comprising etanercept in the truncated form at positions S186 and D235, TNFR-Fc fusion protein in an active form and aggregate, disulfide scrambled TNFR-Fc, etc. The same peak pattern is also disclosed in Korean patent No. 10-1454316, which relates to a method for preparing an active form of TNFR-Fc fusion protein by using a method for producing a recombinant protein. Meanwhile, hydrophobic interaction chromatography conventionally used for isolating TNFR-Fc fusion protein is merely designed to obtain high purity of an active form of TNFR-Fc fusion protein by removing and minimizing impurities except active forms of TNFR-Fc fusion protein, such as aggregates, disulfide-scrambled TNFR-Fc fusion protein, and truncated forms of TNFR-Fc fusion protein.

Meanwhile, a biosimilar is a material which is equivalent to existing approved products in terms of quality, safety, and efficacy, and specifically, only when it has a constitution similar to an originator product thereof in terms of ingredients and content of impurities, it can be used as a biomedical product. For example, etanercept (Pfizer) contains approximately 9% to 18% of the ingredient having low bioactivity which is disclosed as a component of hydrophobic interaction chromatography peak 3 (hereinafter, "peak 3") in the conventional art, and which may have influence on pharmacology as well as potency. Accordingly, developing a biosimilar product requires adjusting the content of peak 3 to a level similar to that of the originator product. Although there is a method for purifying a sample including TNFR-Fc prepared using HIC by a conventional method for producing recombinant proteins (Korean patent No. 10-1454316), the method is merely designed to obtain high purity of a peak 2 ingredient, which is an active form of TNFR-Fc after removing impurities. There has been no trial for adjusting the content of peak 3, which is a type of impurity having low bioactivity, to a level similar to that of an originator product.

DETAILED DESCRIPTION OF THE INVENTION

Technical Problem

The present inventors have made efforts to develop a method for preparing TNFR-Fc fusion protein containing a specific content of peak 3 through adjustment in producing TNFR-Fc fusion protein using hydrophobic interaction chromatography. As a result, they confirmed that TNFR-Fc fusion protein whose peak 3 content is adjusted to a level similar to conventional originator products can be produced by pre-equilibrating a hydrophobic interaction chromatograph (HIC) medium containing an aromatic functional group with an equilibration buffer comprising a predetermined concentration of sodium chloride, and loading and eluting a sample, thereby completing the present invention.

Technical Solution

An object of the present invention is to provide a method for preparing a TNFR-Fc fusion protein mixture containing a target content of hydrophobic chromatogram peak 3, and a method for adjusting a content of hydrophobic chromatogram peak 3.

Advantageous Effects

The present invention provides a method for producing a TNFR-Fc fusion protein by using hydrophobic interaction chromatography, wherein a target content of hydrophobic chromatogram peak 3 is included by adjusting a content of hydrophobic chromatogram peak 3 by conducting hydrophobic interaction chromatography through equilibration with an equilibration buffer comprising a predetermined concentration of sodium chloride or ammonium sulfate. Accordingly, the disclosed method can be instrumentally applied for preparation of biomedical products comprising recombinant proteins such as etanercept which is produced by genetic recombination technique from animal cell culture.

BRIEF DESCRIPTION OF DRAWING

FIG. 1 illustrates a chromatogram of an HIC Flow-Through process using Phenyl Sepharose High Performance resin according to an Example of the present invention.

PREFERRED EMBODIMENT OF THE INVENTION

As an aspect of the present invention to solve the above technical problem, the present invention provides a method for preparing a TNFR-Fc fusion protein mixture containing a target content of hydrophobic chromatogram peak 3.

The method is preferably performed comprising (a) injecting a sample containing a TNFR-Fc fusion protein mixture liquid produced from mammalian cells into a column filled with hydrophobic interaction chromatography (HIC) medium comprising an aromatic functional group, which is pre-equilibrated with an equilibration (EQ) buffer comprising sodium chloride or ammonium sulfate; and (b) collecting an eluate by eluting the protein with an elution buffer comprising sodium chloride or ammonium sulfate at the same concentration as that of the equilibration buffer.

When the TNFR-Fc fusion protein is produced by a host cell transformed with an expression vector comprising a polynucleotide encoding the TNFR-Fc fusion protein, cysteines of TNFR protein bind with each other at random, and thus they do not form disulfide bonds identical to those of a native TNFR protein, or TNFR protein is also partially truncated, and thus fails to form a correct TNFR-Fc dimer, in addition to the formation of a dimer form of TNFR-Fc fusion protein that binds to TNF-α and shows a biological activity. These ingredients are shown as isolated peaks in the hydrophobic chromatogram, and the existing research has defined them as peaks 1 to 3, respectively. Each peak has been confirmed as including a truncated form of protein, an active form of protein, and other aggregates, or ingredients having low bioactivity such as disulfide-scrambled TNFR-Fc. These TNFR-Fc fusion proteins including etanercept are sold as blockbuster pharmaceutical products. However, conventionally approved products for sale and for a clinical purpose contain 9% to 18% of peak 3, which may have influence on potency and/or pharmacology. In particular, for biosimilar products to be approved, equivalence to existing approved or originator products is required. Further, differences in the impurity content resulting from preparation processes such as isolation and purification processes which are used for producing biosimilars are likely to influence efficacy of the pharmaceutical products, and thus equally adjusting the hydrophobic interaction chromatography peak 3 content is crucial. However, when TNFR-Fc fusion proteins are produced by using the recombinant protein production method, the content of each ingredient provided is not consistent, and cannot be adjusted. Accordingly, rather than merely removing ingredients having low bioactivity through processes purifying a mixture including various types of TNFR-Fc fusion proteins, a method for adjusting the content of such ingredients to a consistent level is required. Said method of the present invention can be instrumentally applied for purifying an active form of TNFR-Fc fusion proteins to contain a target content of hydrophobic interaction chromatography peak 3 including aggregates, disulfide-scrambled TNFR-Fc fusion proteins, etc. in isolating the active form of TNFR-Fc fusion proteins from a mixture of TNFR-Fc fusion proteins by using hydrophobic interaction chromatography.

Through said method, the present invention has found for the first time that while hydrophobic interaction chromatography (HIC) has conventionally been used only for removing impurities, in the case where a sample containing a TNFR-Fc fusion protein mixture liquid produced from mammalian cells is equilibrated with salts at various concentrations, particularly sodium chloride, the hydrophobic interaction chromatography peak 3 content can be adjusted at a targeted level. This finding has not been reported.

As used herein, the term "TNFR (tumor necrosis factor receptor) protein" means a receptor protein binding to TNF-α. The TNFR protein includes TNFRI(p55) protein or TNFRII(p75) protein, preferably may be a TNFRII protein, but not limited thereto. The TNFRII may be interchangeable with TNFRSF1B (tumor necrosis factor receptor superfamily member 1B). The TNFRII protein may be a TNFRII protein having 4 domains and a transmembrane region and comprises 235 amino acids, but not limited thereto. Information about the TNFRI protein and TNFRII protein may be obtained from the known databases such as US NIH GenBank, and for example, it may be a protein having Accession number NP_001056 or P20333, but is not limited thereto.

The TNFR protein has a biological activity of binding to TNF-α, of which overexpression in the human body is known to cause various diseases, and thus it can be used for the treatment of TNF-α-mediated diseases such as autoimmune diseases. To achieve this, the immunoglobulin Fc region is fused with TNFR protein to prepare a fusion protein having increased half-life.

As used herein, the term "TNFR (tumor necrosis factor receptor)-Fc fusion protein" means a product resulting from linkage of the entire or a part of TNFR protein with immunoglobulin Fc region by enzymatic action, or resulting from expression of two polypeptides into a single polypeptide by gene manipulation. In the TNFR-Fc fusion protein, the TNFR protein and the immunoglobulin Fc region may be directly linked with each other, or linked via a peptide linker, but is not limited thereto. For example, TNFR-Fc fusion proteins may include etanercept.

The TNFR-Fc fusion protein may be prepared by fusion of the entire or a part of TNFR protein with the immunoglobulin Fc region, and for example, by fusion of the amino acids from 1 to 235 positions of TNFRII protein with 232 amino acids of the immunoglobulin Fc region including a hinge region, but is not limited thereto. In addition, the TNFR-Fc fusion protein may be codon-optimized for expression in the host cells. For example, the TNFR-Fc fusion protein may be a TNFR-Fc fusion protein codon-optimized for CHO cells, defined by the amino acid sequence of SEQ ID NO: 1, but is not limited thereto. The TNFR-Fc fusion protein includes a protein comprising the amino acid sequence of SEQ ID NO: 1, and all proteins having amino acid sequences having 70% or higher homology, preferably 80% or higher homology, more preferably 90% or higher homology, much more preferably 95% or higher homology, and most preferably 98% or higher homology with the sequence, as long as the proteins substantially have an activity of binding to TNF-α. It is apparent that any type of protein variants having a deletion, modification, substitution, or addition of some sequence may be within the scope of the present invention, as long as the sequence having the homology is an amino acid sequence having a biological activity that is substantially identical or corresponding to the TNFR (tumor necrosis factor receptor)-Fc fusion protein. In addition, the polynucleotide encoding the TNFR (tumor necrosis factor receptor)-Fc fusion protein includes a nucleotide sequence of SEQ ID NO: 2, and all nucleotide sequences having 70% or higher homology, preferably 80% or higher homology, more preferably 90% or higher homology, much more preferably 95% or higher homology, and most preferably 98% or higher homology with the sequence, as long as the nucleotide sequences substantially encode proteins having an activity of binding to TNF-α. It is also apparent that any type of nucleotide sequences encoding protein variants having a deletion, modification, substitution, or addition of some sequence may be within the scope of the present invention, as long as the sequence having the homology is a nucleotide sequence encoding an amino acid sequence having a biological activity that is substantially identical or corresponding to the TNFR-Fc fusion protein. In one embodiment of the present invention, codon was specifically optimized for CHO cells.

As used herein, the term "immunoglobulin (Ig) Fc region" refers to a part of immunoglobulin that includes the heavy-chain constant region 2 (CH2), the heavy-chain constant region 3 (CH3), and a hinge region, excluding the variable regions of the heavy and light chains, the heavy-chain constant region 1 (CH1) and the light-chain constant region 1 (CL1) of the immunoglobulin. The immunoglobulin Fc region of the present invention includes a native amino acid sequence, and a sequence derivative thereof. An amino acid sequence derivative is a sequence that is different from the native amino acid sequence due to a deletion, an insertion, a non-conservative, or conservative substitution or combinations thereof of one or more amino acid residues. In addition, the immunoglobulin Fc region may be a Fc region that is derived from IgG, IgM, IgE, IgA, or IgD, or that is made by combinations thereof or hybrids thereof. Preferably, it is derived from IgG, which is known to enhance the half-life of binding proteins. More preferably, it is derived from IgG1, but is not limited thereto.

On the other hand, the term "combination", as used herein, means that polypeptides encoding single-chain immunoglobulin Fc regions of the same origin are linked to a single-chain polypeptide of a different origin to form a dimer or multimer. That is, a dimer or multimer may be formed from two or more fragments selected from the group consisting of IgG Fc, IgA Fc, IgM Fc, IgD Fc, and IgE Fc fragments.

As used herein, the term "hybrid", as used herein, means that sequences encoding two or more immunoglobulin Fc regions of different origin are present in a single-chain immunoglobulin Fc region. In the present invention, various types of hybrids are possible. That is, domain hybrids may be composed of one to four domains selected from the group consisting of CH1, CH2, CH3, and CH4 of IgG Fc, IgM Fc, IgA Fc, IgE Fc, and IgD Fc, and may include the hinge region. On the other hand, IgG is also divided into IgG1, IgG2, IgG3, and IgG4 subclasses, and the present invention includes combinations and hybrids thereof.

The TNFR-Fc fusion protein may be obtained by introducing the expression vector comprising the polynucleotide encoding the fusion protein into mammalian cells, and by then expressing it therein.

In the present invention, the pCUCBin-mSig-TNFcept vector was used as the representative expression vector comprising the polynucleotide encoding the TNFR-Fc fusion protein, and transformed into CHO cells to express the TNFR-Fc fusion protein. The mixture of various forms of TNFR-Fc fusion proteins such as the active TNFR-Fc fusion protein, the truncated forms of TNFR-Fc fusion protein, the inactive TNFR-Fc fusion protein, or/and the TNFR-Fc fusion protein aggregate, etc. are included in the TNFR-Fc fusion proteins obtained by the above method. Therefore, it is necessary to purify the inactive form of TNFR-Fc fusion protein as well as the active form thereof to be contained at a predetermined ratio. When the preparation method of the present invention is used, the content of peak 3 comprising fragments, the active fusion protein, purified aggregates, etc., and thus a target content of peak 3 can be adjusted.

Generally, culture broth of mammalian cells further contains various proteins and the like in addition to a targeted protein. In order to remove such proteins, a sample containing a TNFR-Fc fusion protein mixture preferably produced from the mammalian cells may be prepared by being partially purified by affinity chromatography, anion chromatography, or both.

In a specific Example of the present invention, affinity chromatography was conducted with culture broth of transfected CHO cells, anion chromatography was conducted with the eluate therefrom, and then the eluate therefrom was used as the sample.

As an example, medium filling a column used in the hydrophobic interaction chromatography may include a phenyl group as an aromatic functional group. In a specific Example of the present invention, a column filled with Phenyl Sepgarose High Performance resin produced by GE Healthcare is used, but is not limited thereto.

In an embodiment, a target content of hydrophobic chromatogram peak 3 may be 9% to 18%. As a specific example, if the hydrophobic chromatogram peak 3 content of the TNFR-Fc fusion protein mixture of said step (a) exceeds 20%, the peak 3 content can be lowered to approximately 9% to 18% by application of the method of the present invention and purification.

In an embodiment, said equilibration and elution buffers may comprise 7 mM to 15 mM sodium phosphate. In a specific Example of the present invention, a buffer containing 10 mM sodium phosphate is used, but is not limited thereto.

In an embodiment, said equilibration and elution buffers may have a pH of 6 to 8.5. A buffer having a pH beyond said range may cause denaturation of a target protein, and accordingly may be difficult to be used in hydrophobic interaction chromatography of recombinant protein.

In an embodiment, the preparation method of the present invention is characterized by adjusting the concentration of sodium chloride of the equilibration buffer according to the target content of hydrophobic chromatogram peak 3, wherein when the target content of hydrophobic chromatogram peak 3 is in a range of 2% to 17%, an equilibration buffer comprising sodium chloride at a concentration of 1 M to 1.4 M is used for the equilibration. Specifically, for a loading sample having the peak 3 content of 21%, using an equilibration buffer comprising 1.1 M sodium chloride enables the peak 3 content to fall to a range of 5.3% to 17%, using an equilibration buffer comprising 1.2 M sodium chloride enables the peak 3 content to fall to a range of 2.9% to 15.7%, using an equilibration buffer comprising 1.3 M sodium chloride enables the peak 3 content to fall to a range of 2.5% to 14.8%, and using an equilibration buffer comprising 1.4 M sodium chloride enables the peak 3 content to fall to a range of 2.2% to 13.7%.

Further, the preparation method of the present invention is characterized by adding ammonium sulfate of the equilibration buffer according to the target content of hydrophobic chromatogram peak 3, wherein when the hydrophobic chromatogram peak 3 content of the sample exceeds 45%, an equilibration buffer comprising ammonium sulfate at a concentration of 0.45 M to 0.55 M is used for the equilibration.

In an embodiment, when culture broth obtained by a method for producing recombinant proteins contains hydrophobic chromatogram peak 3 excessively, e.g., in a range of exceeding 45%, the hydrophobic chromatogram peak 3 content can be lowered to approximately 10% by conducting hydrophobic interaction chromatography using the aforementioned equilibration buffer containing sodium chloride after lowering the peak 3 content to a range of 20% to 30% by conducting hydrophobic interaction chromatography followed by the equilibration with an equilibration buffer containing ammonium sulfate.

The hydrophobic interaction chromatography can be conducted by sequential processes consisting of loading, equilibration, stripping, and cleaning in place (CIP).

The stripping process is conducted to separate and elute all proteins remaining on the column, and buffers whose constitution is identical to the equilibration buffer excluding sodium chloride and ammonium sulfate may be used in the process.

CIP is a process for managing devices in a safe and cost-efficient manner in producing biomedical products, and enables efficient removal of impurities from chromatography medium and reuse thereof. The CIP may be conducted by using 0.5 N sodium hydroxide solution, but is not limited thereto. CIP may be repeated many times as needed, but is not limited thereto.

In another aspect, the present invention provides a method for adjusting a content of hydrophobic chromatogram peak 3 contained in etanercept, comprising: pre-equilibrating a hydrophobic interaction chromatography medium with an equilibration buffer comprising sodium chloride at a concentration of 1.0 M to 1.5 M or ammonium sulfate at a concentration of 0.45 M to 0.55 M; and loading a sample comprising a TNFR-Fc fusion protein prepared to have the same salt concentration as that of the pre-equilibrated hydrophobic interaction chromatography medium.

In an embodiment, as aforementioned, the equilibration buffer has a pH of 6 to 8.5.

The method of the present invention using an equilibration buffer comprising sodium chloride or ammonium sulfate is characterized by the peak 3 content of the final product adjusted to decrease compared with that of a loaded sample.

In an embodiment, the peak 3 content of the sample whose peak 3 content exceeds 20% may be decreased to a level of 2% to 17% by using an equilibration buffer comprising sodium chloride.

In an embodiment, the peak 3 content of the sample whose peak 3 content exceeds 45% is decreased to a level of 18% or less by using an equilibration buffer comprising ammonium sulfate.

DETAILED DESCRIPTION OF EMBODIMENTS OF THE INVENTION

Hereinafter, the present invention will be described in more detail with reference to Examples. However, these Examples are for illustrative purposes only, and the invention is not intended to be limited by these Examples.

Example 1: Preparation of Etanercept and HIC Flow-Through

In order to prepare etanercept, the pCUCBin-mSig-TNF-cept vector including a gene encoding the TNFR-Fc fusion protein into CHO cells was transfected and cultured, and then affinity chromatography and anion chromatography were sequentially applied to culture broth of CHO cells selected by using MTX.

Specifically, affinity chromatography has been conducted as follows: a XK26 column (GE Healthcare) filled with MabSelect SuRe™ (GE Healthcare), which is an affinity resin, has been equilibrated by being sufficiently washed with a buffer containing 20 mM Tris-HCl, pH 8.0, has been bound to the affinity resin by being washed with the prepared culture broth, and then has been eluted with an elution buffer at pH 3.0 to pH 3.4. The pH of the eluate has been adjusted to pH 7.0 to 8.0 by using 2 M Tris.

With the eluate obtained by the above affinity chromatography, anion chromatography has been conducted as follows: a LRC15 column (Pall Life Sciences) filled with Fractogel EMD TMAE (Merck), which is an anion resin, has been equilibrated by being sufficiently washed with a buffer containing Tris at pH 7.5 to 8.5, has been bound to the anion resin by being washed with the eluate obtained from the affinity chromatography, and then has been eluted with a Tris elution buffer containing 100 mM to 200 mM sodium chloride.

The HIC Flow-Through process which was applied to the eluate obtained by conducting the affinity chromatography and anion chromatography sequentially is set forth below. The peak 3 content obtained in the process has been measured using a linear gradient with buffer A (0.1 M sodium phosphate, pH 6.0, 1.8 M ammonium) and buffer B (0.1 M sodium phosphate, pH 6.0).

Experimental Example 1: Adjustment of Peak 3 Content Using Sodium Chloride

For the HIC Flow-Through process, EQ buffers containing 1.1 M to 1.4 M sodium chloride in 10 mM sodium phosphate have been prepared, and EQ buffer was adjusted to pH 6.3. Further, samples loaded in HIC have been prepared to include sodium phosphate and sodium chloride at the same concentration as that of the EQ buffer.

A HIC Flow-Through process using Phenyl Sepharose High Performance resin (GE Healthcare) consists of processes of loading, equilibration, stripping, and CIP as illustrated in FIG. 1, and 10 mM sodium phosphate at pH 6.3 and 0.5 N sodium hydroxide were used as buffers for stripping and CIP, respectively.

The eluate has been monitored by being collected at 50 mAU or more on the basis of absorbance at 280 nm to collect fractions by 5 column volume (CV) to be the EQ buffer, and Table 1 illustrates concentrations of sodium chloride using the resultants.

TABLE 1

| Conditions of Equilibration Buffer | Peak 3 Content (%) |
| --- | --- |
| Loaded Sample | 21 |
| 10 mM sodium phosphate pH 6.3, 1.1M sodium chloride | 5.3 to 17.0 |
| 10 mM sodium phosphate pH 6.3, 1.2M sodium chloride | 2.9 to 15.7 |
| 10 mM sodium phosphate pH 6.3, 1.3M sodium chloride | 2.5 to 14.8 |
| 10 mM sodium phosphate pH 6.3, 1.4M sodium chloride | 2.2 to 13.7 |

As illustrated in Table 1, as a concentration of sodium chloride in use increases, the peak 3 content has shown the decreasing tendency, and as a result, it has been confirmed that the peak 3 content can be adjusted in a range of 2.2% to 17.0% according to a concentration of sodium chloride in use.

Experimental Example 2: Adjustment of Peak 3 Content Using Ammonium Sulfate

For the HIC Flow-Through process using ammonium sulfate, EQ buffer containing 0.5 M sodium sulfate in a buffer containing 20 mM Tris-HCl at pH 8.0 was prepared. Further, samples loaded in HIC have been prepared to contain 20 mM Tris-HCl at pH 8.0 and 0.5 M ammonium sulfate.

A HIC Flow-Through process has been conducted with a XK16 column (GE Healthcare) filled with Phenyl Sepharose High Performance resin (GE Healthcare) by 5 cm. As in Experimental Example 1, the process consists of processes of loading, equilibration, stripping, and CIP, and 20 mM Tris-HIC at pH 7.0 and 0.5 N sodium hydroxide were used as buffers for stripping and CIP, respectively.

The eluate has been monitored by being collected at 50 mAU or more on the basis of absorbance at 280 nm to collect fractions by 5 column volume (CV) to be the EQ buffer, and as a result, when a HIC Flow-Through process has been conducted with a loaded sample containing 46.1% of peak 3, the peak 3 content after the process has been confirmed to have been adjusted to a level of 12%.

The invention claimed is:

1. A method for preparing a TNFR-Fc fusion protein mixture comprising a target content of hydrophobic chromatogram peak 3 impurities, wherein the TNFR-Fc fusion protein mixture is a biosimilar to an originator product and the target content of hydrophobic chromatogram peak 3 impurities is adjusted to that of the originator product TNFR-Fc fusion protein mixture, comprising:

(a) injecting a sample comprising a TNFR-Fc fusion protein mixture liquid produced from mammalian cells into a column filled with hydrophobic interaction chromatography (HIC) medium comprising an aromatic functional group, which is pre-equilibrated with an equilibration (EQ) buffer comprising sodium chloride at a concentration of 1 M to 1.4 M or ammonium sulfate at a concentration of 0.45 M to 0.55 M; and (b) adjusting the content of hydrophobic chromatogram peak 3 impurities by eluting the protein mixture with an elution buffer comprising sodium chloride or ammonium sulfate at the same concentration as that of the equilibration buffer, wherein the concentration of sodium chloride or ammonium sulfate is adjusted to produce the target content of hydrophobic chromatogram peak 3 impurities, wherein the content of the hydrophobic chromatogram peak 3 impurities of the sample comprising said TNFR-Fc fusion protein mixture of step (a) exceeds 20%, and wherein the target content of hydrophobic chromatogram peak 3 impurities is 9% to 18%.

2. The method of claim 1, wherein the aromatic functional group is a phenyl group.

3. The method of claim 1, wherein the equilibration and elution buffers comprise 7 mM to 15 mM sodium phosphate.

4. The method of claim 1, wherein the equilibration and elution buffers have a pH of 6 to 8.5.

5. The method of claim 1, wherein the concentration of sodium chloride of the equilibration buffer is adjusted to produce the target content of hydrophobic chromatogram peak 3 impurities, wherein when the content of hydrophobic chromatogram peak 3 impurities of the sample is in a range of exceeding 20% to less than or equal to 45% and the target content of hydrophobic chromatogram peak 3 impurities is in a range of 2% to 17%, an equilibration buffer comprising sodium chloride at a concentration of 1 M to 1.4 M is used for the equilibration.

6. The method of claim 1, wherein the concentration of ammonium sulfate of the equilibration buffer is adjusted to produce the target content of hydrophobic chromatogram peak 3 impurities, wherein when the content of the hydrophobic chromatogram peak 3 impurities of the sample exceeds 45% and the target content of the hydrophobic chromatogram peak 3 impurities is in a range of 10% to 20%, an equilibration buffer comprising ammonium sulfate at a concentration of 0.45 M to 0.55 M is used for the equilibration.

7. The method of claim 1, wherein the sample comprising a TNFR-Fc fusion protein mixture liquid produced from mammalian cells is partially purified by affinity chromatography, anion chromatography, or both.

8. The method of claim 1, wherein the hydrophobic interaction chromatography consists of sequential processes of loading, equilibration, stripping, and cleaning in place (CIP).

9. A method for adjusting a content of hydrophobic chromatogram peak 3 contained in etanercept, comprising:
pre-equilibrating a hydrophobic interaction chromatography medium with an equilibration buffer comprising sodium chloride at a concentration of 1.0 M to 1.5 M or ammonium sulfate at a concentration of 0.45 M to 0.55 M; and
loading a sample comprising a TNFR-Fc fusion protein prepared to have the same salt concentration as that of the pre-equilibrated hydrophobic interaction chromatography medium;
wherein the content of the hydrophobic chromatogram peak 3 is adjusted to decrease as compared with the loaded sample, and
wherein the hydrophobic chromatogram peak 3 content of a sample with a hydrophobic chromatogram peak 3 content exceeding 20% is decreased to a level of 2% to 17%.

10. The method of claim 9, wherein the equilibration buffer comprising sodium chloride has a pH of 6 to 8.5.

11. The method of claim 10, wherein the hydrophobic chromatogram peak 3 content of the sample whose hydrophobic chromatogram peak 3 content exceeds 45% is decreased to a level of 10% to 20%.

12. A method for preparing a biosimilar TNFR-Fc fusion protein mixture comprising a target content of hydrophobic chromatogram peak 3 impurities, comprising:
 (a) determining the amount of hydrophobic chromatogram peak 3 impurities in an originator product comprising a TNFR-Fc fusion protein mixture,
 (b) injecting a sample of a biosimilar product comprising a TNFR-Fc fusion protein mixture liquid produced from mammalian cells into a column filled with hydrophobic interaction chromatography (HIC) medium comprising an aromatic functional group, which is pre-equilibrated with an equilibration (EQ) buffer comprising sodium chloride or ammonium sulfate; and
 (c) adjusting the level of hydrophobic chromatogram peak 3 impurities by eluting the TNFR-Fc fusion protein mixture with an elution buffer comprising sodium chloride or ammonium sulfate at the same concentration as that of the equilibration buffer,
 wherein said target content of hydrophobic chromatogram peak 3 impurities is adjusted to that of said originator product, wherein the amount of hydrophobic impurities in the eluate is adjusted by adjusting the concentration of sodium chloride or ammonium sulfate in the elution buffer, and wherein the target content of hydrophobic chromatogram peak 3 impurities in said originator product is between 9% to 18%.

* * * * *